United States Patent [19]

Salter et al.

[11] Patent Number: 5,584,285

[45] Date of Patent: Dec. 17, 1996

[54] BREATHING CIRCUIT APPARATUS FOR A NEBULIZER

[75] Inventors: Peter W. Salter; James Chua, both of Tehachapi, Calif.

[73] Assignee: Salter Labs, Arvin, Calif.

[21] Appl. No.: 485,880

[22] Filed: Jun. 7, 1995

[51] Int. Cl.⁶ .................................................. A61M 11/00
[52] U.S. Cl. ............................... 128/200.21; 128/202.27; 128/203.23
[58] Field of Search ........................ 128/200.11–200.23, 128/207.14, 202.21, 202.27, 203.12, 203.21, 203.23, 204.13

[56] References Cited

U.S. PATENT DOCUMENTS

| | | | |
|---|---|---|---|
| Re. 30,046 | 7/1979 | van Amerongen | 239/338 |
| Re. 33,717 | 10/1991 | Svoboda | 239/338 |
| 2,723,055 | 11/1955 | Beard, Jr. | 222/402.2 |
| 2,826,454 | 3/1958 | Coanda | 239/338 |
| 3,097,645 | 7/1963 | Lester | 128/200.21 |
| 3,580,249 | 5/1971 | Takaoka | 128/200.14 |
| 3,591,090 | 7/1971 | Carden | 239/305 |
| 3,658,059 | 4/1972 | Steil | 128/200.21 |
| 3,744,722 | 7/1973 | Burns | 239/338 |
| 3,762,409 | 10/1973 | Lester | 128/200.14 |
| 3,838,686 | 10/1974 | Szekely | 128/200.18 |
| 3,918,451 | 11/1975 | Steil | 128/203.21 |
| 4,333,450 | 6/1982 | Lester | 128/200.14 |
| 4,454,877 | 6/1984 | Miller et al. | 128/200.21 |
| 4,461,425 | 7/1984 | Miller | 239/338 |
| 4,470,412 | 9/1984 | Nowacki et al. | 128/200.18 |
| 4,512,341 | 4/1985 | Lester | 128/200.21 |
| 4,529,003 | 7/1985 | Iannuzzelli et al. | 137/493.8 |
| 4,560,519 | 12/1985 | Cerny | 261/78 A |
| 4,566,452 | 1/1986 | Farr | 128/200.21 |
| 4,588,129 | 5/1986 | Shanks | 239/338 |
| 4,598,704 | 7/1986 | Bordoni et al. | 128/200.14 |
| 4,657,007 | 4/1987 | Carlin et al. | 128/200.18 |
| 4,703,753 | 11/1987 | Bordoni et al. | 128/200.14 |

(List continued on next page.)

FOREIGN PATENT DOCUMENTS

| | | | |
|---|---|---|---|
| 483193 | 5/1977 | Australia | 128/200.21 |
| 439361 | 1/1927 | Germany | 128/200.21 |
| 22150 | 11/1961 | Germany | 128/200.16 |
| 3434111 | 3/1986 | Germany | 128/200.16 |
| 446276 | 7/1975 | U.S.S.R. | 128/200.18 |
| 86/01731 | 3/1986 | WIPO | 128/200.21 |

OTHER PUBLICATIONS

Pari Respiratory Equipment, Inc. Brochure for "Pari LC Plus Nebulizer" 4 pages, Jul., 1994.

*Primary Examiner*—V. Millin
*Assistant Examiner*—Eric P. Raciti
*Attorney, Agent, or Firm*—Shoemaker and Mattare, Ltd.

[57] ABSTRACT

A breathing circuit apparatus used with a nebulizer device that generates an aerosol is adapted for use by a user for inhaling the aerosol through the user's nose and/or mouth and thereafter exhaling exhalation gas through the breathing circuit apparatus. The breathing circuit apparatus includes a container, an inlet valve, an outlet valve and a user connection port. The container defines an interior chamber therein and is coupled to the nebulizer device. The inlet valve is connected to the container and includes an air inlet port for one-way air flow of ambient air into the interior chamber. The inlet valve moves between a closed condition to prevent the ambient air from entering into the interior chamber and an opened condition to permit the ambient air to enter into the interior chamber. The outlet valve is connected to the container and includes a gas exhalation port for one-way gas flow of the exhalation gas. The outlet valve moves between a closed state to prevent exhalation gas from exiting the interior chamber and an opened state to permit exhalation gas to exit from the interior chamber. The user connection port is in fluid communication with the interior chamber and the user's nose and/or mouth when the user inhales and exhales. As the user inhales the aerosol from the interior chamber, the inlet valve is opened and the outlet valve is closed. As the user exhales, the inlet valve is closed and the outlet valve is opened to allow the exhalation gas to exit the interior chamber and discharge into the exterior ambient air.

5 Claims, 8 Drawing Sheets

U.S. PATENT DOCUMENTS

| | | | |
|---|---|---|---|
| 4,746,067 | 5/1988 | Svoboda | 239/338 |
| 4,792,097 | 12/1988 | Kremer, Jr. et al. | 239/338 |
| 4,886,055 | 12/1989 | Hoppough | 128/200.14 |
| 4,907,581 | 3/1990 | King | 128/200.18 |
| 5,054,477 | 10/1991 | Terada et al. | 128/200.14 |
| 5,062,419 | 11/1991 | Rider | 128/200.21 |
| 5,165,392 | 11/1992 | Small, Jr. | 128/200.18 |
| 5,170,782 | 12/1992 | Kocinski | 128/200.16 |
| 5,209,225 | 5/1993 | Glenn | 128/200.14 |
| 5,280,784 | 1/1994 | Kohler | 128/200.14 |
| 5,287,847 | 2/1994 | Piper et al. | 128/200.21 |
| 5,309,900 | 5/1994 | Knoch et al. | 128/200.14 |
| 5,312,046 | 5/1994 | Knoch et al. | 239/338 |

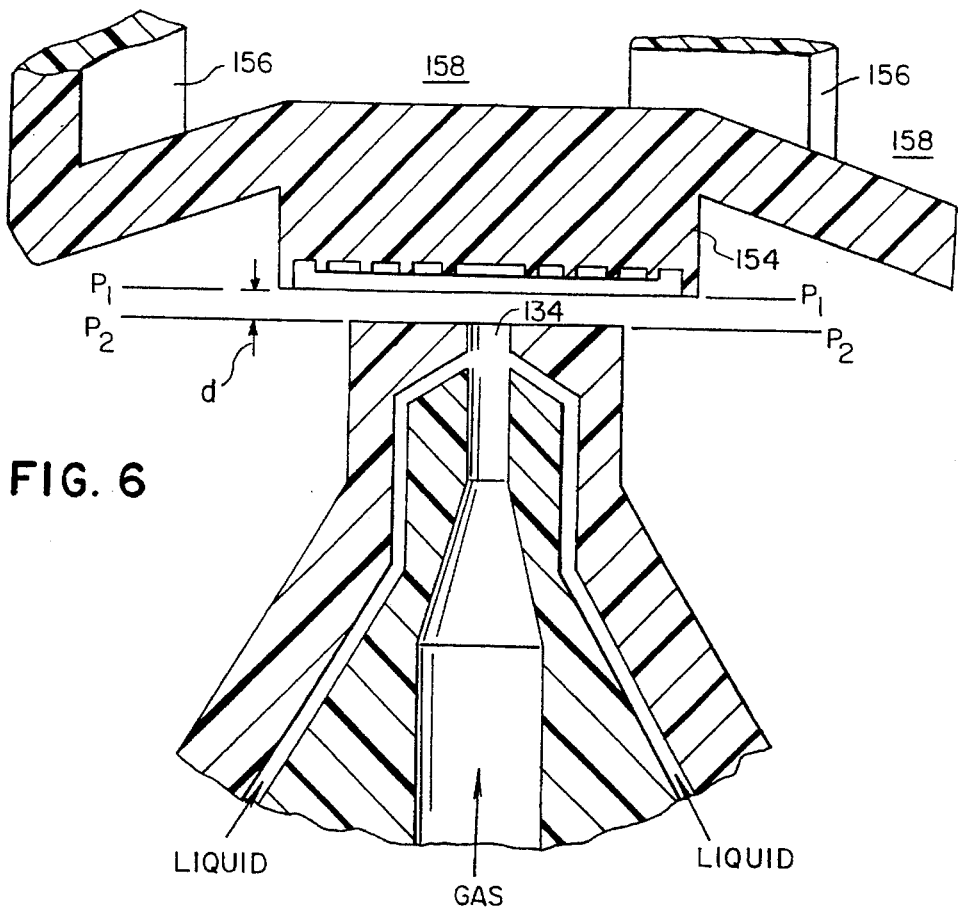
FIG. 6
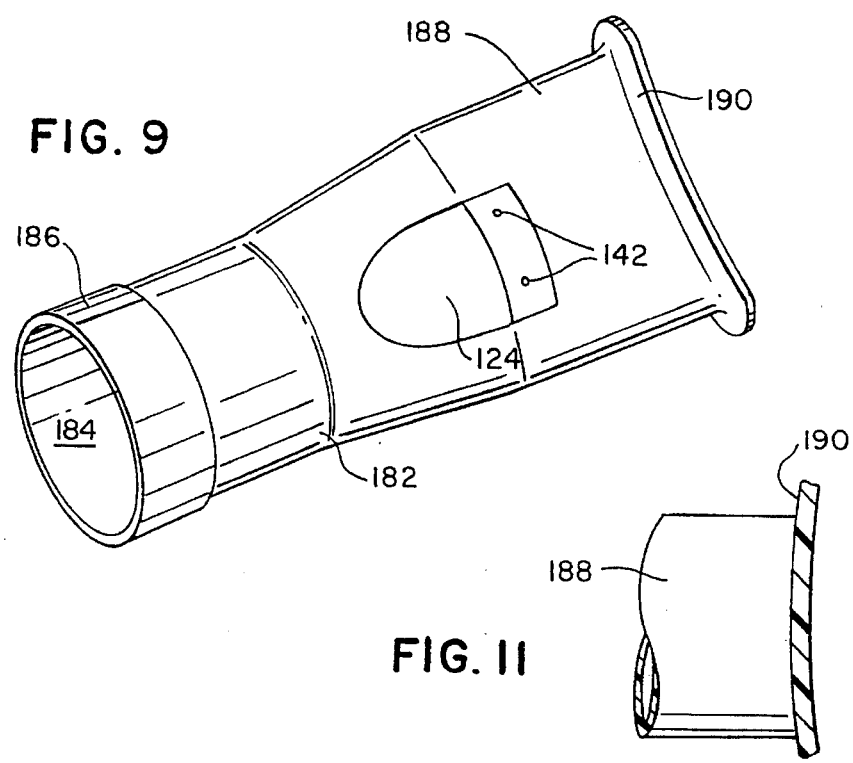
FIG. 9
FIG. 11

BREATHING CIRCUIT APPARATUS FOR A NEBULIZER

FIELD OF THE INVENTION

The present invention relates to a breathing circuit apparatus adapted for use with a nebulizer device so that a user can inhale an aerosol generated by the nebulizer device from the breathing circuit apparatus. More particularly, the present invention is directed to a breathing circuit apparatus adapted for use with a nebulizer device that generates a medicament-containing aerosol so that a breathing user/patient can inhale the medicinal aerosol from the breathing circuit apparatus and subsequently exhale exhalation gas through the breathing circuit apparatus.

BACKGROUND OF THE INVENTION

Various types of nebulizers have been used in commerce for a variety of applications and are well known in the art. One common application for a nebulizer is in the medical industry. Such a nebulizer has been used in the medical industry for effective delivery of medicines to a patient's lungs. An example of a nebulizer capable of delivering medicine to a patient's lungs is disclosed in U.S. Pat. No. 4,746,067 to Steven A. Svoboda which is incorporated herein by reference and is generally introduced as prior art in FIG. 1.

This prior art nebulizer is a device for aerosolizing a liquid medicine 7 with a pressurized gas (the source of which is not shown) which is typically compressed air. The prior art nebulizer includes a container 1 for holding liquid medicine 7, a mixing mechanism 50 and a deflector member 11. Mixing mechanism 50 comprises a venturi tube 2 and a liquid conduit means 6. Venturi tube 2 has an upstream opening 3 adapted for connection to the source of pressurized gas, a throat portion 4 and a discharge opening 5. Liquid conduit means 6 is connected to container 1 and has an outlet opening 8 adjacent to a downstream end 9 of throat portion 4. Venturi tube 2 is dimensioned and positioned to withdraw liquid medicine 7 from reservoir 19 and through liquid conduit means 6 and to project a mixture of liquid and gas out of discharge opening 5 at a high velocity in a nebulized liquid/gas stream.

A deflector member 11 is positioned adjacent to and disposed from discharge opening 5 of venturi tube 2 and has a surface 12 intersecting the liquid/gas stream and causing a dispersion of the liquid/gas stream in a second direction different from the first direction. Deflector member 11 is employed to further reduce the liquid droplet size in the nebulized liquid/gas stream thereby causing a fine mist which dispersed about an interior chamber of container 1.

With the prior art being replete with nebulizers, some other nebulizers are described in U.S. Pat. No. 5,287,847 to Piper et al., U.S. Pat. No. 5,209,225 to Glenn, U.S. Pat. No. 4,657,007 to Calin et al., U.S. Pat. No. 4,588,129 to Shanks, U.S. Pat. No. 4,512,341 to Lester, U.S. Pat. No. 3,762,409 to Lester, U.S. Pat. No. 3,744,722 to Burns and U.S. Pat. No. 3,097,645. In one form or another, all of these patents as well as other prior art nebulizers teach a nebulizer device which mixes a pressurized aerosolizing gas with a liquid to produce a stream of nebulized liquid and gas predicated upon the commonly known venturi principle. Often, this stream is directed to a deflector member which further reduces the size of the liquid droplets in the nebulized liquid stream to form a fine mist. The mist disperses throughout the interior chamber of the nebulizer. Particularly in light of the patents noted above, the fine mist of nebulized liquid is inhaled by the user through a tube opened to the ambient air environment. Prior art nebulizers continuously produce the fine mist. Thus, during exhalation, some of the fine mist which typically contains costly medicament exits the container through the tube and into the ambient air environment. This results in wasted medicament.

There is a need in the industry for a breathing circuit apparatus which can be used in combination with a nebulizer device operative to generate an aerosol so that the user can inhale aerosol through his/her nose and/or mouth from the breathing circuit apparatus and thereafter can exhale exhalation gas through the breathing circuit apparatus and into ambient environment. It would be advantageous if the breathing circuit apparatus used in combination with a nebulizer device can create a preselected amount of positive back-pressure on the lungs when the user exhales through the breathing circuit apparatus. In this latter regard, it would also be advantageous if the breathing circuit apparatus included an adjustable outlet valve so that the amount of positive back-pressure on the lungs can be regulated, or be provided with a flapper valve with preselected stiffness for providing back-pressure of from about 5 cm to about 20 cm of water. There is also a need in the industry for breathing circuit apparatus used with a nebulizer device that minimizes loss of aerosolized medicament into the ambient environment to minimize waste of the medication contained in the aerosol and limit contamination of the atmosphere with medicament. It would be advantageous if the aerosolized medicament can be contained in the breathing circuit apparatus as much as possible, particularly during exhalation, so that a health care provider can better provide medicament dosage requirements for the user/patient. It would be further advantageous if the breathing circuit apparatus adapted for use with the nebulizer device has a mouthpiece structure.

With a breathing circuit apparatus adapted for both inhalation and exhalation by the patient, it would be desirable if the breathing circuit apparatus include a drool trap which prevents the user's saliva from contaminating the medicament-containing liquid which is used to generate the aerosolized medicament. It would also be advantageous if the breathing circuit apparatus has an inlet which could be utilized for replenishing the liquid in the nebulizer device without interruption of use or monitoring breathing pressure in the breathing circuit apparatus while in use. The inlet could further be utilized as a sensing port for monitoring breathing cycles and pressures generated by the user/patient to control the timing of the flow of aerosolizing gas to the nebulizer device to occur during only pre-selected intervals during the user/patient's breathing cycles. The present invention satisfies these needs and provides these advantages.

OBJECTS AND SUMMARY OF THE INVENTION

An object of the present invention is to provide a new and improved breathing circuit apparatus adapted for use in combination with a nebulizer device operative to generate an aerosol so that a user can inhale the aerosol through an opening, i.e. nose and/or mouth, in the user's respiratory system and into the user's lungs and thereafter exhaling exhalation gas from the opening in the user's respiratory system, through the breathing circuit apparatus and into ambient environment.

Another object of the present invention is to provide a breathing circuit apparatus in combination with a nebulizer device that creates a positive back-pressure on the lungs when the user exhales through the breathing circuit apparatus which, in turns, results in a desirable effect of prolonged expansion of the alveoli of the lungs, thus improving absorption of the aerosol into the user's body.

Still another object of the present invention is to provide a breathing circuit apparatus with an adjustable outlet valve so that the amount of positive back-pressure on the lungs can be regulated.

Yet another object of the present invention is to provide a breathing circuit apparatus with a nebulizer device that minimizes loss of aerosolized medicament into the ambient air, thus minimizing waste of the medication contained in the aerosol.

Yet a still further object of the present invention is to provide a breathing circuit apparatus with a nebulizer device that better enables a health care professional to provide a greater density of aerosolized medication for the patient per liter of air inhaled.

A still further object of the present invention is to provide a breathing circuit apparatus with a nebulizer device having a mouthpiece structure.

Yet another object of the present invention is to provide a breathing circuit apparatus with a nebulizer device having a drool trap which prevents the user's saliva from contaminating the medicament-containing liquid which is used to generate the aerosolized medicament.

A still further object of the present invention is to provide a breathing circuit apparatus having an inlet which could be utilized for a variety of reasons such as replenishing the liquid in the nebulizer without interruption of use and monitoring breathing pressure in the nebulizer while in use.

Yet another object of the present invention is to provide a breathing circuit apparatus with a nebulizer device having an inlet which could be utilized as a sensing port for monitoring breathing cycles and pressures generated by the user/patient to control the timing of the flow of aerosolizing gas to the breathing circuit apparatus to occur during only pre-selected intervals during the user/patient's breathing cycles.

Accordingly, a breathing circuit apparatus of the present invention is hereinafter described. In combination with a nebulizer device operative to generate an aerosol, the breathing circuit apparatus of the present invention is adapted for use by a user for inhaling the aerosol through an opening, i.e. nose and/or mouth, in a respiratory system of the user and into the user's lungs and thereafter exhaling exhalation gas from the nose and/or mouth of the user and through the breathing circuit apparatus. In its broadest form, the breathing circuit apparatus includes a container, an inlet valve, and outlet valve and a user connection. The container defines an interior chamber therein and is coupled to the nebulizer device. The container has an inlet orifice formed therethrough to provide fluid communication between the interior chamber and the nebulizer device. The interior chamber is sized and adapted to receive the aerosol generated by the nebulizer device through the inlet orifice.

The inlet valve is connected to the container and including an air inlet port for one-way air flow of ambient air disposed exteriorly of the container into the interior chamber. The inlet valve is operative to move between a closed condition to prevent the ambient air from entering into the interior chamber and an opened condition to permit the ambient air to enter into the interior chamber.

The outlet valve is connected to the container and includes a gas exhalation port for one-way gas flow of the exhalation gas from the user's respiratory system after inhalation. The outlet valve is operative to move between a closed state to prevent exhalation gas from exiting the interior chamber and an opened state to permit exhalation gas to exit from the interior chamber.

The user connection port is operative to be disposed between and in fluid communication with the interior chamber and the opening into the user's respiratory system when the user inhales and exhales. As the user inhales the aerosol from the interior chamber, the inlet valve is in the opened condition while simultaneously therewith the outlet valve is in the closed state so that the aerosol is inhaled into the lungs of the user without loss of the aerosol to the exterior ambient air. As the user exhales the exhalation gas from the user's respiratory system with at least a threshold amount of exhalation gas pressure and through the user connection port, the inlet valve is in the closed condition while simultaneously therewith the outlet valve is in the opened state to allow the exhalation gas to exit the interior chamber and discharge into the exterior ambient air. The threshold amount of exhalation gas pressure creates a positive back-pressure on the user's lungs.

The breathing circuit apparatus of the present invention includes a downdraft tube extending within the interior chamber to define a downdraft duct. The downdraft tube has a first end connected to the container which surrounds the air inlet port of the inlet valve and a free second end which is disposed opposite of the first end. When exterior ambient air enters through the air inlet port at the first end when the inlet valve is in the opened condition, the ambient air flows through the downdraft duct to the free second end.

The breathing circuit apparatus of the present invention also includes a deflector member that is disposed within the interior chamber and interposed between the free second end of the downdraft tube and the inlet orifice. The deflector member is positioned in a spaced apart relationship from the free second end of the downdraft tube and the inlet orifice. The deflector member and the inlet orifice are spaced apart from one another at a distance selected from a range between approximately 0.019 millimeters and 0.036 millimeters.

The breathing circuit apparatus of the present invention includes a plurality of spacers. The plurality of spacers interconnect the free second end of the downdraft tube and the deflector member and define spacer openings between sequential ones of the spacers. When the ambient air enters the container through the inlet valve, the ambient air passes through the downdraft duct and outwardly therefrom through the spacer openings.

The container of the breathing circuit apparatus of the present invention can be either unitary in construction or can be formed of two sections, an upper container section and a lower container section releasably connected to the upper container section. The upper container section includes a lower rim portion having a plurality of channels formed therein. The lower container section includes an upper rim portion having a plurality of dogs projecting radially outwardly therefrom. Respective ones of the dogs and the channels are sized and adapted for matable engagement with each other so that the upper container section and the lower container section can be releasably connected together in a fluid tight relation to form a unitary container.

The container includes an outlet conduit assembly having a conduit stem connected to and extending outwardly from an outer container wall of the container to form a conduit stem region of the interior chamber and a mouthpiece structure with a cross-member. A first mouthpiece end of the mouthpiece structure is sized and adapted to be slidably received into the conduit stem region. The outlet conduit assembly also includes a drool trap formed within the conduit stem region. The container also includes an inlet which is formed therethrough to provide fluid communication into the interior chamber. A plug sized and adapted to be removably received by the inlet.

Although it is preferred that the breathing circuit apparatus of the present invention be used in combination with the nebulizer device, the breathing circuit apparatus can also stand alone without the nebulizer device. Thus, other applications of the breathing circuit apparatus of the present invention are possible without departing from the spirit of the inventive concepts disclosed herein. In this case, in lieu of a user connection port, the breathing circuit apparatus comprises an opened port which is formed into the container and is in fluid communication with the interior chamber and the ambient air environment.

These and other objects of the present invention will become more readily appreciated and understood from consideration of the following detailed description of the exemplary embodiments of the present invention when taken in conjunction with the accompanying drawings, in which:

BRIEF DESCRIPTION OF THE DRAWINGS

FIG. 6 is an enlarged fragmentary side view in cross-section of the nebulizer device disposed within an interior chamber and positioned in a facially-opposing, spaced-apart, parallel relationship with a deflector member;

FIG. 9 is a perspective view of a mouthpiece structure;

FIG. 11 is a fragmentary side view partially in cross-section of a cross-member of the mouthpiece structure taken along line 11—11 in FIG. 10.

DETAILED DESCRIPTION OF THE EXEMPLARY EMBODIMENTS

Figure 1:
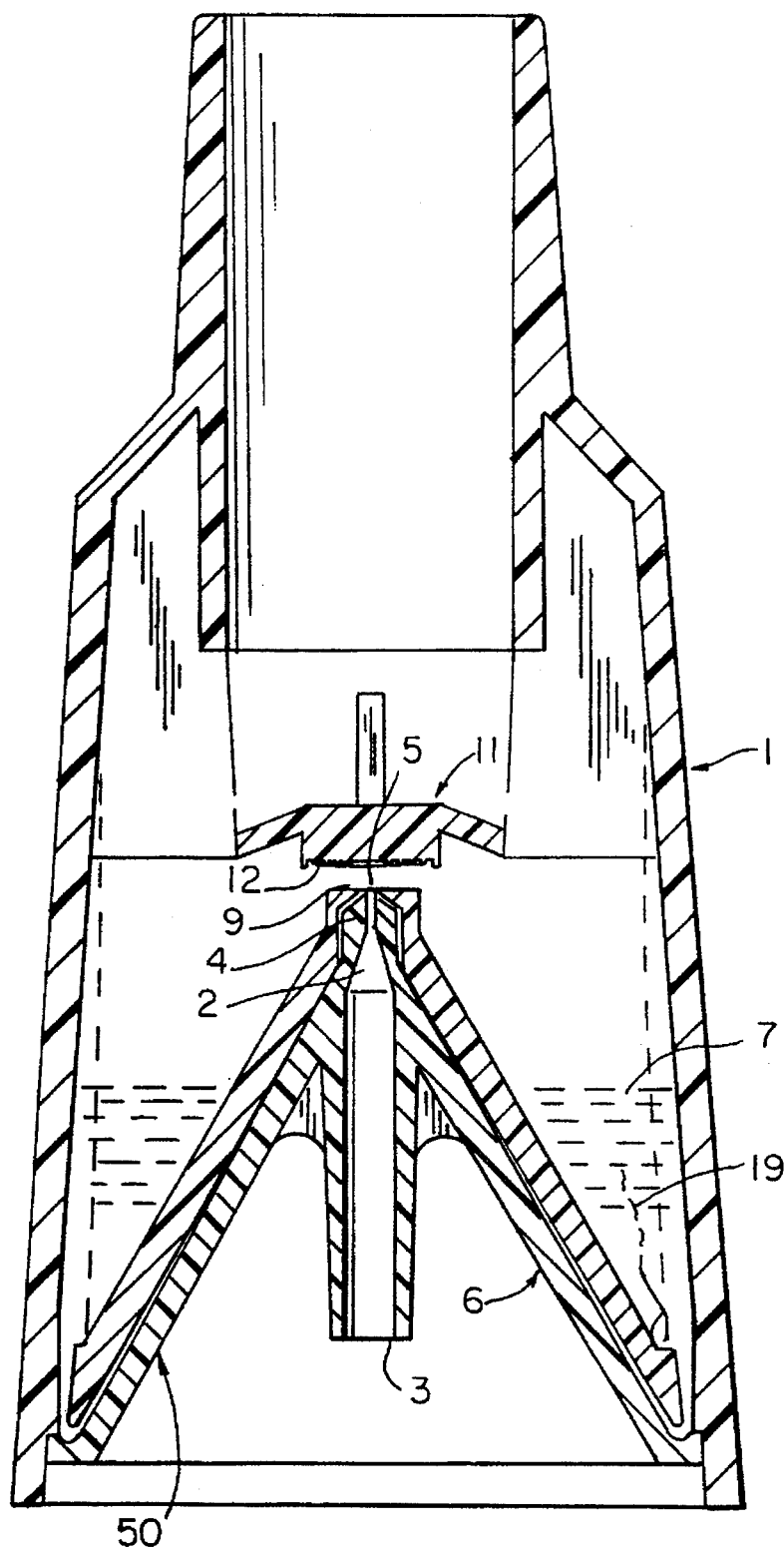
FIG. 1 is a side elevational view in cross-section of a prior art nebulizer.

A breathing circuit apparatus of the present invention used in combination with a nebulizer device which produces aerosol is adapted for use by a user for inhaling the aerosol through an opening, i.e. nose and/or mouth in a respiratory system of the user and into the user's lungs and thereafter exhaling exhalation gas from the opening in the user's respiratory system and through the breathing circuit apparatus. One of ordinary skill in the art would appreciate that many different types of nebulizer devices exist that produce an aerosol for many different types of applications. Furthermore, a skilled artisan would appreciate that nebulizer devices are often employed in the medical industry to produce a medicament-containing aerosol from a liquid medicament for inhalation by a user/patient. As the description proceeds, the skilled artisan would appreciate that the breathing circuit apparatus of the present invention can be utilized in combination with any type of nebulizer device that produces an aerosol regardless if the aerosol produced contains medicament. Additionally, the breathing circuit apparatus of the present invention can either incorporate the nebulizer device into its structure as a unitary construction or be utilized separately from the nebulizer device but operatively coupled thereto. Only by way of example and not of limitation, the breathing circuit apparatus of the present invention is described and illustrated hereinafter with components of a prior art nebulizer discussed hereinabove and understood by one of ordinary skill in the art. Further discussion of these prior art components is deemed unnecessary.

A first exemplary embodiment of a breathing circuit apparatus 110 of the present invention is generally introduced in FIGS. 2–11. With reference to FIGS. 2 and 3, a first exemplary embodiment of breathing circuit apparatus 110 is used in combination with a nebulizer device 112 which is formed as a unitary construction with breathing circuit apparatus 110 and is operably coupled to an aerosolizing pressurized gas source 114. Nebulizer device 112 is operative to generate an aerosol at gas pressures of from about 20 psi to 50 psi at a flow rate of 6 to 8 liters per minute. Breathing circuit apparatus 110 is adapted for use by a user 116 for inhaling the aerosol through an opening 118, the user's mouth, in a respiratory system of user 116 and into the user's lungs and thereafter exhaling exhalation gas from opening 118 in the user's respiratory system and through breathing circuit apparatus 110. Breathing circuit apparatus comprises a container 120, an inlet valve 122, an outlet valve 124 and a user connection port 126.

Container 120, generally cylindrical in shape, defines an interior chamber 128 therein. For the first embodiment of breathing circuit apparatus 110 interior chamber 128 includes a reservoir region 130 which holds the liquid to be nebulized and an aerosol region 132 for receiving the aerosol after the liquid becomes nebulized. Container 120 is operatively coupled to nebulizer device 112 having an inlet orifice 134 which provides fluid communication between interior chamber 128 and nebulizer device 112. At least reservoir region 130 of interior chamber 128 is sized and adapted to receive the aerosol generated by nebulizer device 112 through inlet orifice 134.

As best shown in FIGS. 3–6, inlet valve 122 is connected to container 120 and includes an air inlet port 136 which provides for one-way air flow of ambient air (represented by solid arrow "a" in FIG. 4) disposed exteriorly of container 120 into interior chamber 128. Inlet valve 122 is operative to move between a closed condition (FIG. 5) to prevent the ambient air "a" from entering into interior chamber 128 and an opened condition (FIG. 4) to permit the ambient air "a" to enter into interior chamber 128. Outlet valve 124 is connected to container 120 and includes a gas exhalation port 138 for one-way gas flow of the exhalation gas (represented by dashed arrow "b" in FIG. 5) from the user's respiratory system after inhalation by user 116. Outlet valve 124 is operative to move between a closed state (FIG. 4) to prevent exhalation gas "b" from exiting interior chamber 128 and an opened state to permit exhalation gas "b" to exit from interior chamber 128.

Figure 4:
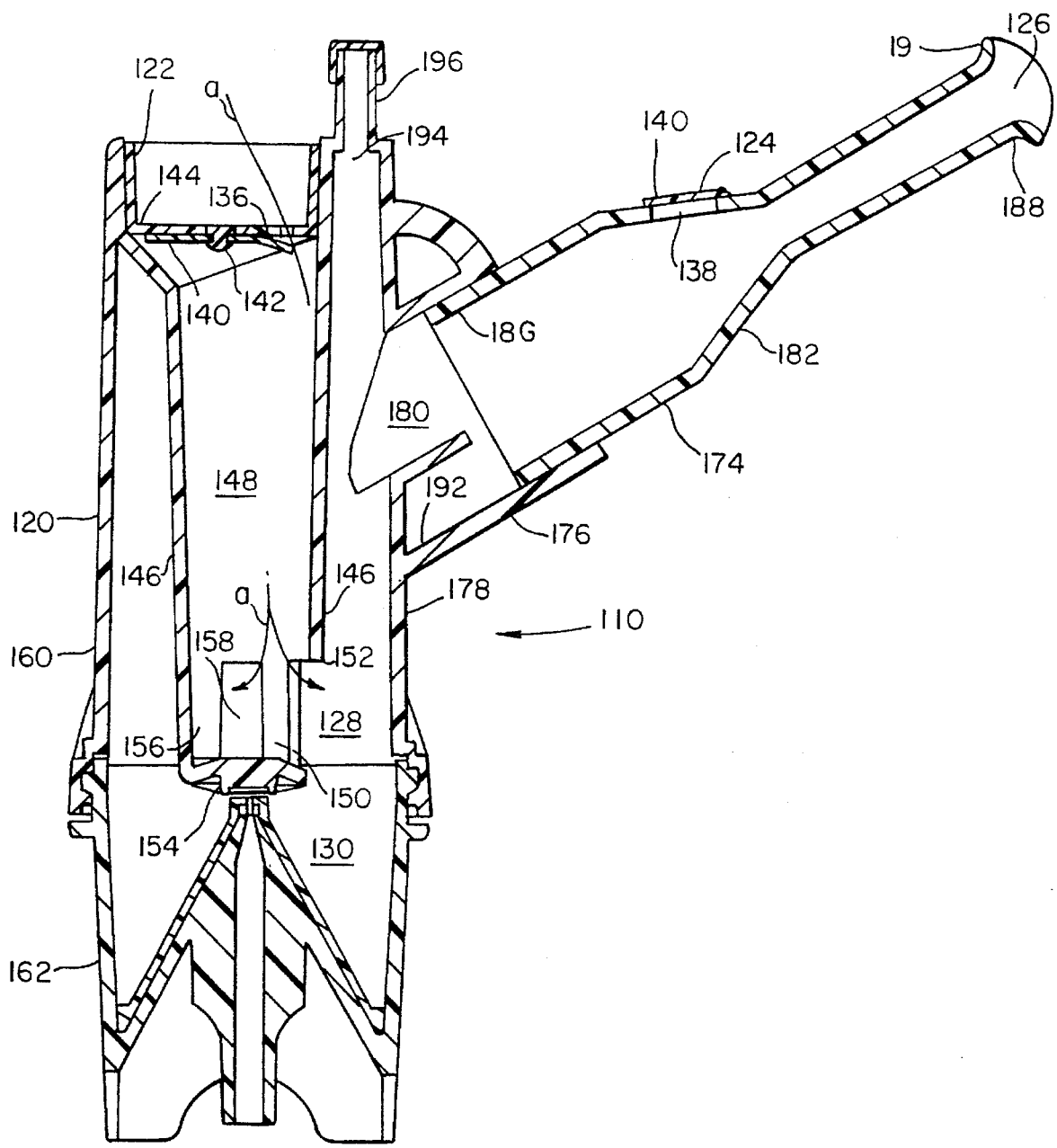
FIG. 4 is a side view in cross-section of the breathing circuit apparatus of the present invention showing an inlet valve having an air inlet port being in an opened condition and an outlet valve having an outlet port being in a closed state.
Figure 5:
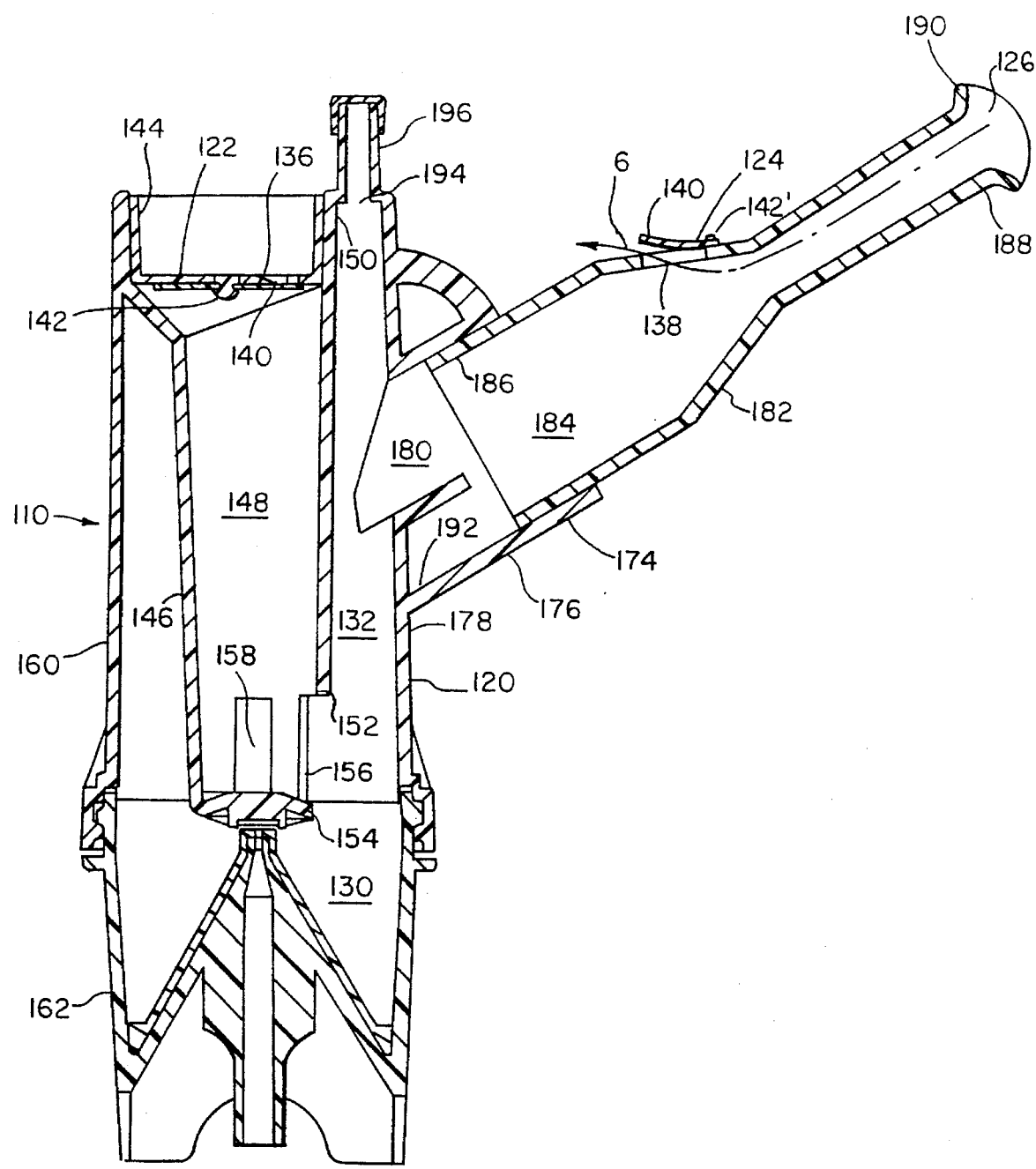
FIG. 5 is a side view in cross-section of the breathing circuit apparatus of the present invention showing the inlet valve with its air inlet port being in a closed condition and an outlet valve with its outlet port being in an opened state.
Figure 7:
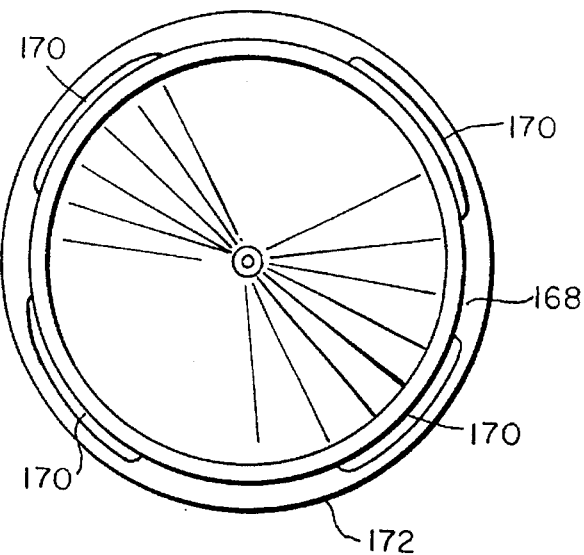
FIG. 7 is a top plan view of a lower section of the breathing circuit apparatus of the present invention taken along line 7—7 of FIG. 3 and showing a plurality of dogs.
Figure 8:
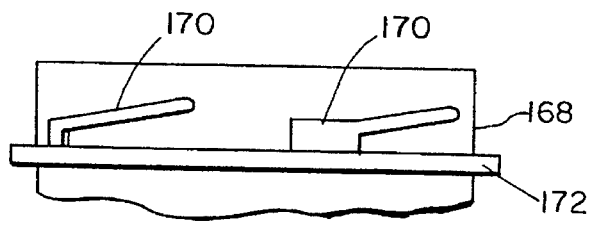
FIG. 8 is a fragmentary side view in elevation of the lower section of the breathing circuit apparatus of the present invention showing the plurality of dogs of FIG. 7.

User connection port 126 is operative to be disposed between and in fluid communication with interior chamber 128 and the opening 118, i.e. the user's nose and/or mouth, into the user's respiratory system when user 116 inhales and exhales. As user 116 inhales the aerosol from interior chamber 128, inlet valve 122 is in the opened condition while simultaneously therewith outlet valve 124 is in the closed state as shown in FIG. 4. When this occurs, the aerosol is inhaled into the lungs of user 116 without loss of the aerosol to the exterior ambient air. As user 116 exhales the exhalation gas "b" from the user's respiratory system and through user connection port 126 with at least a threshold amount of exhalation gas pressure, thereby creating a positive back-pressure on the user's lungs, inlet valve 122 is in the closed condition while simultaneously therewith outlet valve 124 is in the opened state to allow the exhalation gas "b" to exit interior chamber 128 and discharge into the exterior ambient air as shown in FIG. 5.

Figure 10:
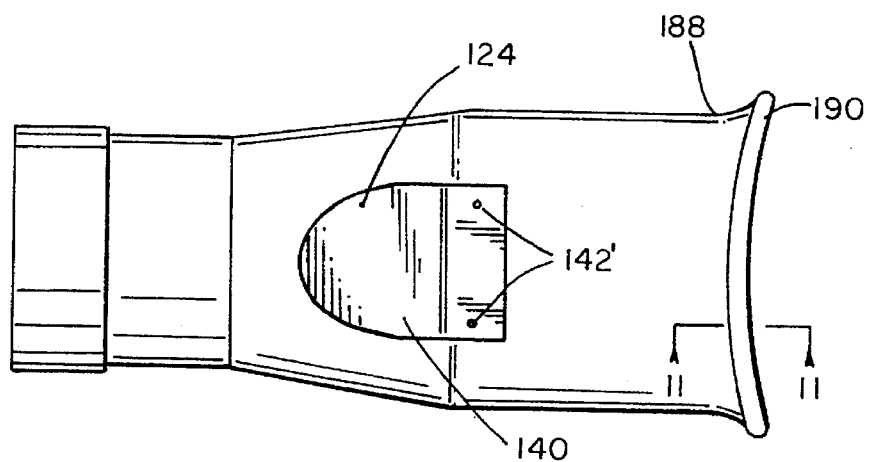
FIG. 10 is a top plan view of the mouthpiece structure shown in FIG. 9.

Again with reference to FIG. 3, inlet valve 122 is normally disposed in the closed condition and, likewise, outlet valve 124 is normally disposed in the closed state. Specifically, inlet valve 122 is resiliently biased in the normally closed condition and outlet valve 124 is resiliently biased in the normally closed state. It is preferred that each of inlet valve 122 and outlet valve 124 is a flap valve having a flap 140 which is fabricated from a stiff yet resilient material normally used for flap valves such as rubber or plastic. Although not by way of limitation, rivet 142 retains flap 140 onto a valve housing 144 for inlet valve 122 while rivet 142' retains flap 140 over gas exhalation port 138 of outlet valve 124. Depending upon thickness and selection of the flap material, the amount of pressure required to open inlet valve 122 and outlet valve 124 can vary. Thus, by way of example, the exhalation gas pressure can be varied by changing the resistance to flow described, thus enabling more effective usage by the patient of medicament-containing aerosol, because of the resultant increase in the time required for patient exhalation. The efficacy of the aerosolized medicament is improved by this longer exposure to the patient's expanded lungs. Typically, resistance to exhalation should be in the range of from about 5 cm to 20 cm of water pressure during normal exhalation.

As best shown in FIGS. 3–5, breathing circuit apparatus 110 includes a downdraft tube 146 which extends within interior chamber 128 to define a downdraft duct 148. Downdraft tube 146 includes a first end 150 and a free second end 152. First end 150 is connected to container 120 and surrounds air inlet port 136 of inlet valve 122. Free second end 152 is disposed opposite of first end 150 so that, as illustrated in FIG. 4, exterior ambient air "a" enters through air inlet port 136 at first end 150 when inlet valve 122 is in the opened condition and flows through downdraft duct 148 to free second end 152.

In FIGS. 3–6, breathing circuit apparatus 110 includes a deflector member 154 which is disposed within interior chamber 128 and is interposed between free second end 152 of downdraft tube 146 and inlet orifice 134. Deflector member 154 is positioned in a spaced apart relationship from free second end 152 of downdraft tube 146 and inlet orifice 134. For the first exemplary embodiment of the breathing circuit apparatus of the present invention, deflector member 154 and inlet orifice 134 are spaced apart from one another at a distance "d" shown in FIG. 6 which is selected from a range between approximately 0.019 millimeters and 0.036 millimeters. To best describe the orientation of inlet orifice 134 relative to deflector member 154, inlet orifice 134 defines a first imaginary plane "$P_1$" while deflector member 154 defines a second imaginary plane "$P_2$". Preferably, first imaginary plane "$P_1$" and second imaginary plane "$P_2$" are facially opposed to and parallel with one another.

Again, with reference to FIGS. 2–6, breathing circuit apparatus 110 includes a plurality of spacers 156. The plurality of spacers 156 interconnect free second end 152 of downdraft tube 146 and deflector member 154. Additionally, the plurality of spacers define spacer openings 158 which are located between sequential ones of spacers 156. As best illustrated in FIG. 4, when the ambient air "a" enters container 120 through inlet valve 122, the ambient air "a" passes through downdraft duct 148 and outwardly therefrom through spacer openings 158.

Although not by way of limitation, container 120 comprises an upper container section 160 and a lower container section 162 which is releasably connected to upper container section 160. Particularly as shown in FIGS. 3, 7 and 8, upper container section 160 includes a lower rim portion 164 having a plurality of channels 166 formed therein. Also, lower container section 162 includes an upper rim portion 168 having a plurality of dogs 170 projecting radially outwardly from upper rim portion 168. As commonly known in the industry, respective ones of dogs 170 and channels 166 are sized and adapted for matable engagement with each other so that upper container section 160 and lower container section 162 can be releasably connected together in a fluid tight relation to form a unitary container. An annular rim element 172 extends circumferentially about and projects radially outwardly from upper rim portion 168 of lower container section 162.

As shown in FIGS. 3–5, container 120 further includes an outlet conduit assembly 174 that has a conduit stem 176. Conduit stem 176 is connected to and extends outwardly from an outer container wall 178 of container 120 in an upwardly direction relative to lower container section 162. Conduit stem 176 defines a conduit stem region 180 of interior chamber 128. Preferably, conduit stem 176 is generally configured in a cylindrical shape. As best shown in FIGS. 9–11, outlet conduit assembly 174 includes a mouthpiece structure 182 that defines a mouthpiece region 184 of interior chamber 128. It is preferred that mouthpiece structure 182 incorporate outlet valve 124 with its accompanying gas exhalation port 138 thereinto as illustrated by the appropriate figures. Mouthpiece structure 182 has a first mouthpiece end 186 sized and adapted to be slidably received into conduit stem region 180 and a second mouthpiece end 188 that is disposed opposite first mouthpiece end 186 and is connected to a cross-member 190.

Cross-member 190 extends transversely to second mouthpiece end 188. For the first exemplary embodiment of the breathing circuit apparatus of the present invention, cross-member 190 includes user connector port 126. By example only and not limitation, cross-member 190 is arcuate in cross-section and forms a concavity as best illustrated in FIGS. 10 and 11. When breathing circuit apparatus 110 is operative, cross-member 190 is disposed above conduit stem 176 when first mouthpiece end 186 is slidably received by conduit stem region 180.

Further, outlet conduit assembly 174 includes a drool trap 192. Drool trap 192 is formed within conduit stem region 180 by a portion of outer container wall 178 and a bottom portion of conduit stem 176. Since breathing circuit apparatus 110 of the present invention is designed so that user 116 continuously inhales therefrom and exhales thereinto, user 116 may tend to drool into breathing circuit apparatus 110. Drool trap 192 entraps any drool emanating from the user's mouth and prevents the same from contaminating the medicament-containing liquid held in reservoir region 130 of interior chamber 128.

Figure 2:
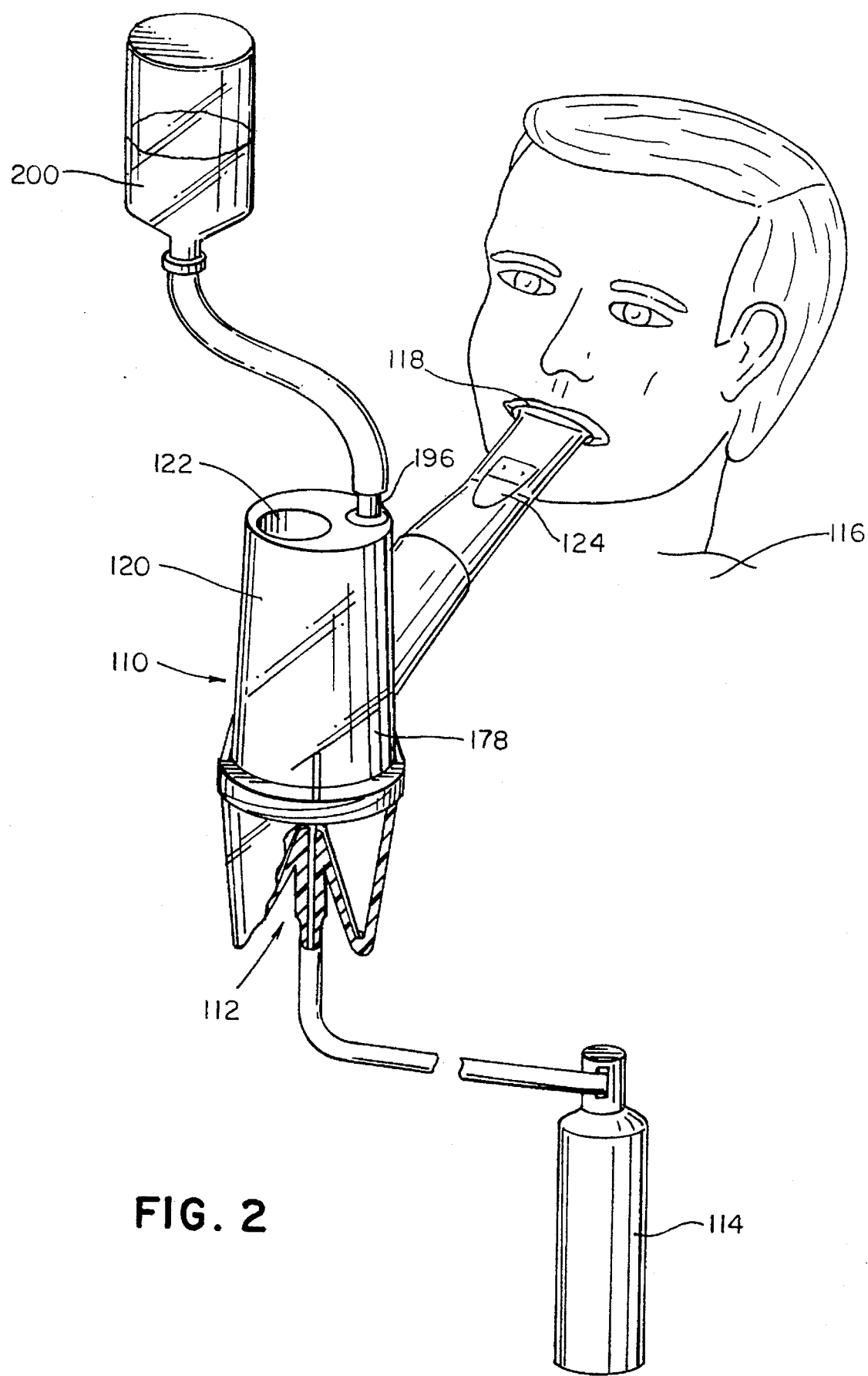
FIG. 2 is a perspective view of a first exemplary embodiment of a breathing circuit apparatus of the present invention partially broken away and illustrated in combination with a nebulizer device shown operatively coupled to a pressurized aerosolizing gas source and a medicament source with a user/patient breathing into and from the breathing circuit apparatus.
Figure 3:
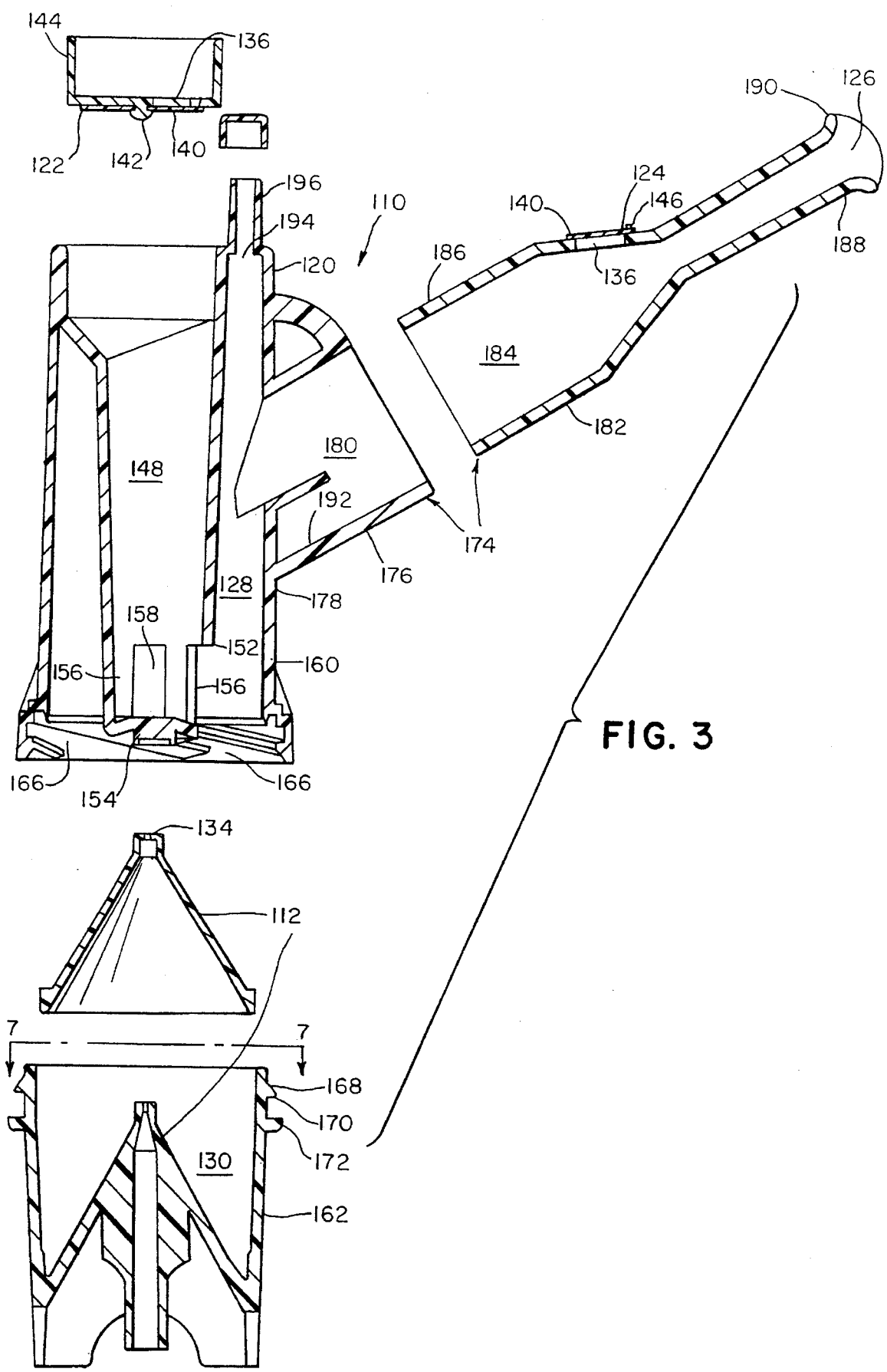
FIG. 3 is an exploded side view in cross-section of the breathing circuit apparatus of the present invention that incorporates a nebulizer device as an integral portion thereof.

Additionally, as shown in FIGS. 2–6, container 120 includes an inlet 194 formed through container 120 to provide fluid communication into interior chamber 128. An inlet tube 196 connects inlet 194 and projects outwardly from container 120. A plug 198 in a form of a cap is sized and adapted to be removably received by either inlet 194 or inlet tube 196 so that when plug 198 is received by inlet 194 or inlet tube 196, fluid communication into interior chamber 128 through inlet 194 or inlet tube 196 is prevented. As illustrated in FIG. 2, one use of inlet 194 is to allow a source of liquid 200 to be coupled in fluid communication with interior chamber 128 so that the liquid can flow into container 120 without interrupting the operation of the breathing circuit apparatus 110 in combination with nebulizer device 112.

Figure 12:
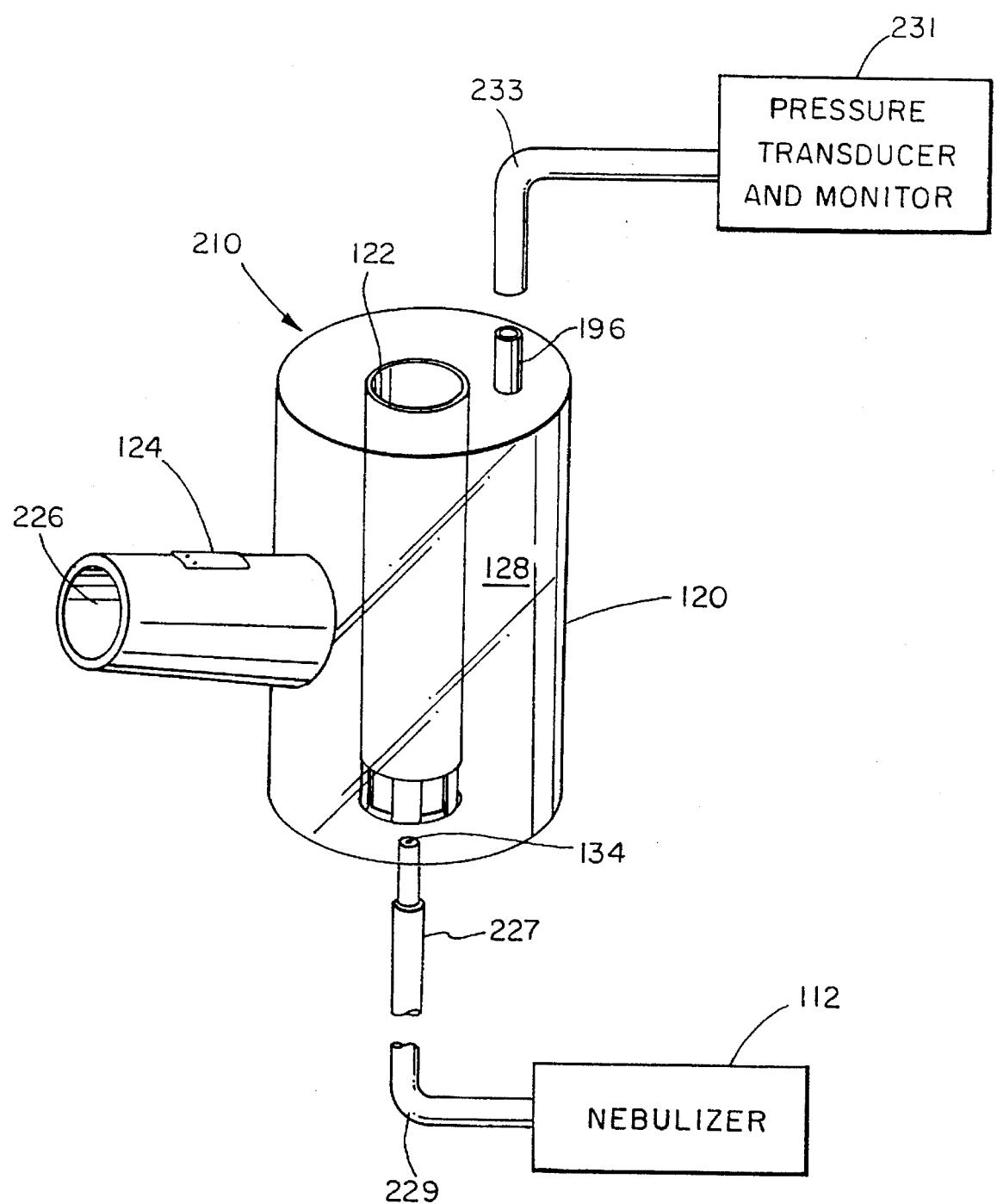
FIG. 12 is a perspective view of a second exemplary embodiment of a breathing circuit apparatus of the present invention shown with a diagrammatic nebulizer and a diagrammatic pressure transducer and monitor.

A second exemplary embodiment of a breathing circuit apparatus 210 of the present invention is shown in FIG. 12. This second exemplary embodiment of breathing circuit apparatus is not integrated as a unitary construction with nebulizer device 112 but stands alone. Breathing circuit apparatus 210 includes container 120, inlet valve 122, outlet valve 124 and an opened port 226. Opened port 225 is formed into container 120 and is in fluid communication with interior chamber 128 and the ambient air environment. Container 120 has inlet orifice 134 formed therethrough. Inlet orifice 134 sized and adapted to conduct a nebulized liquid into interior chamber 128 from nebulizer device 112 which is located remotely from breathing circuit apparatus 210. An inlet orifice tube 227 is coupled in fluid communication with inlet orifice 134 so that aerosol generated by nebulizer device 112 can be conveyed through a nebulizer conduit 229 and into container 120.

A pressure transducer/monitor 231 is coupled in fluid communication with inlet tube 196, utilized as a sensing port, by a monitor conduit 233. With this arrangement, events of pressures occurring in interior chamber 128 as the user inhales and exhales can be monitored, if desired. This information obtained by pressure transducer/monitor 231 can be utilized, for example, to electronically control and electrically operate electrical inlet and outlet valves as well as to electronically control the timing and amounts of aerosol. This sensing port is adapted for monitoring breathing cycles and pressures generated by the user/patient and can control the timing of the flow of aerosolizing gas to the breathing circuit apparatus which can be caused to occur during only pre-selected intervals during the user/patient's breathing cycles.

It is appreciated that the breathing circuit apparatus of the present invention used in combination with the nebulizer can be employed by the user to both inhale the aerosol through his/her nose and/or mouth and exhale exhalation gas through the breathing circuit apparatus and into ambient environment. The outlet valve on the container of the breathing circuit apparatus creates a positive back-pressure on the user's lungs when the user exhales through the breathing circuit apparatus. Back-pressure on the user's lungs is desirable because such back-pressure causes prolonged expansion of the alveoli of the lungs. Prolonged expansion of the alveoli of the lungs results in improved absorption of the medicament-containing aerosol into the user's body. Also, the outlet valve can be adjustable (not shown) so that the amount of positive back-pressure on the lungs can be regulated. With the inlet and outlet valves being normally closed and the breathing circuit apparatus designed to be a "breath-through" device in continuous contact with the user's nose and/or mouth, a minimum amount of aerosolized medicament is lost into the ambient air. As a result, waste of the medication contained in the aerosol is minimized. Furthermore, with minimum waste of medication, health care provider is positioned to better predict medicament dosage requirements for the user/patient.

The breathing circuit apparatus includes several structural features that benefit the user/patient. The mouthpiece structure is designed so that the user/patient can continuously breath through the breathing circuit apparatus. The drool trap prevents the user's saliva from contaminating the medicament-containing liquid. The inlet could be utilized for a variety of reasons such as replenishing the liquid in the nebulizer without interruption of use and monitoring breathing pressure in the nebulizer while in use. Specifically, the inlet can be utilized as a sensing port for monitoring breathing cycles and pressures generated by the user/patient to control the timing of the flow of aerosolizing gas to the breathing circuit apparatus to occur during only pre-selected intervals during the user/patient's breathing cycles.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. In combination with a nebulizer device operative to generate an aerosol, a breathing circuit apparatus adapted for use by a user for inhaling the aerosol through an opening in a respiratory system of the user and into the user's lungs and thereafter exhaling exhalation gas from the opening in the user's respiratory system and through said breathing circuit apparatus, comprising:

(a) a container defining an interior chamber therein and coupled to said nebulizer device having an inlet orifice to provide fluid communication between said interior chamber and the nebulizer device, said interior chamber being sized and adapted to receive the aerosol generated by the nebulizer device through said inlet orifice;

(b) an inlet valve connected to said container and including an air inlet port for one-way air flow of ambient air disposed exteriorly of said container into said interior chamber, said inlet valve operative to move between a closed condition to prevent the ambient air from entering into said interior chamber and an opened condition to permit the ambient air to enter into said interior chamber;

(c) an outlet valve in communication with said container and including a gas exhalation port for one-way gas flow of the exhalation gas from the user's respiratory system after inhalation, said outlet valve operative to move between a closed state and an opened state to permit exhalation gas to exit from said interior chamber; and (d) a user connection port connected to said container and operative to be disposed between and in fluid communication with said interior chamber and the opening into the user's respiratory system when the user inhales and exhales whereby, as the user inhales the aerosol from said interior chamber, said inlet valve is in the opened condition while simultaneously therewith said outlet valve is in the closed state so that the aerosol is inhaled into the lungs of the user without loss of the aerosol to the exterior ambient air and, as the user exhales the exhalation gas from the user's respiratory system and through said user connection port, said inlet valve is in the closed condition while simultaneously therewith said outlet valve is in the opened state to allow the exhalation gas to exit the interior chamber and discharge into the exterior ambient air, and said circuit including a downdraft tube extending within said interior chamber of said container to define a downdraft duct and having a first end connected to said container and surrounding said air inlet port of said inlet valve and a free second end disposed opposite of said first end so that exterior ambient air enters through said air inlet port at said first end when said inlet valve is in the opened condition and flows through said downdraft duct to said free second end.

2. A breathing circuit apparatus according to claim 1 including a deflector member disposed within said interior chamber and interposed between said free second end of said downdraft tube and said inlet orifice, said deflector member positioned in a spaced apart relationship from said free second end of said downdraft tube and said inlet orifice.

3. A breathing circuit apparatus according to claim 2 wherein said deflector member and said inlet orifice are spaced apart from one another at a distance selected from a range between approximately 0.019 millimeters and 0.036 millimeters.

4. A breathing circuit apparatus according to claim 2 wherein said inlet orifice defines a first imaginary plane and said deflector member defines a second imaginary plane, said first and second imaginary planes being facially opposed to and parallel with one another.

5. A breathing circuit apparatus according to claim 2 including a plurality of spacers interconnecting said free second end of said downdraft tube and said deflector member and defining spacer openings between sequential ones of said spacers so that when the ambient air enters said container through said inlet valve, the ambient air passes through said downdraft duct and outwardly therefrom through said spacer openings.

* * * * *